United States Patent [19]
Cambell

[11] Patent Number: 5,479,104
[45] Date of Patent: Dec. 26, 1995

[54] ELECTRICAL SENSOR FOR DETERMINING THE MOISTURE CONTENT OF SOIL

[75] Inventor: Jeffrey E. Cambell, Centerville, Va.

[73] Assignee: Vitel, Inc., Chantilly, Va.

[21] Appl. No.: 120,514

[22] Filed: Sep. 14, 1993

[51] Int. Cl.⁶ ........................... G01R 27/26
[52] U.S. Cl. ............... 324/690; 324/663; 324/664; 73/73
[58] Field of Search ................. 324/663, 664, 324/686, 689, 690; 73/73

[56] References Cited

U.S. PATENT DOCUMENTS

| | | | |
|---|---|---|---|
| 3,581,197 | 5/1971 | Morey, Jr. | 324/690 |
| 4,137,931 | 2/1979 | Hasenbeck | 324/689 X |
| 4,168,466 | 9/1979 | Boldt | 324/664 |
| 4,278,934 | 7/1981 | Ihara et al. | 324/690 |
| 4,278,935 | 7/1981 | Ihara et al. | 324/690 |
| 4,288,742 | 9/1981 | Walsh | 324/690 X |
| 4,540,936 | 9/1985 | Walsh | 324/690 |
| 4,929,885 | 5/1990 | Dishman | 324/664 |

Primary Examiner—Kenneth A. Wieder
Assistant Examiner—Diep Do
Attorney, Agent, or Firm—J. W. Gipple

[57] ABSTRACT

An improved soil moisture sensor and circuitry are described which permit a more compact, simplified, and less expensive integrated unit wherein the essential circuitry of the device is sealed within the sensor head. Determinations of resistance and capacitance are made using a coaxial or other capacitor having spikes or probes which are inserted into the soil or other material.

5 Claims, 3 Drawing Sheets

ELECTRICAL SENSOR FOR DETERMINING THE MOISTURE CONTENT OF SOIL

SUMMARY OF THE INVENTION

The present invention relates to a device which incorporates improved electrical circuitry for use in measuring the moisture content and/or salinity of material into which a sensor is placed.

BACKGROUND OF THE INVENTION

Numerous applications for measuring the moisture content of soils, grains, lumber, and industrial process products exist. A complete sensing system consists of the circuitry and also a probe containing at least two conducting surfaces electrically insulated from each other to form a capacitive structure which can be inserted into the material to be measured. The circuitry is electrically connected to the probe so that an alternating current (AC) stimulus can be applied to one of the probe surfaces while the other surface remains grounded. The circuit output can be used to determine the capacitance and resistance of the sample between the conducting surfaces, which in turn, can be related to the sample conductivity and dielectric constant. Using well know relationships, the sample's moisture content and salinity can be ascertained.

Typically, moisture sensing devices in the past have included a container into which the material is placed, with plates or the like therein for determining the capacitance of the material placed therein and relating that capacitance to the moisture content. For example, the U.S. Pat. No. 3,209,247 to Mead and the U.S. Pat. No. 4,050,016, to Marsh et al show typical devices of this sort. These devices are, however, inconvenient to use since they require removing a portion of the material to be tested. Further, removing the material, for example, by digging a sample of soil, necessarily changes its density so that the measured results are not necessarily the actual moisture content of the soil before its removal.

Another inaccuracy arises in many of these devices because they measure only the capacitance of the soil or measure only the resistance. U.S. Pat. No. 3,803,570 to Barrow et al, for example, describes a capacitance measuring device. None of these capacitance, devices however, have effectively combined high accuracy with ease of use. U.S. Pat. No. 2,870,404 to Oxley describes a resistive measuring device in which a plurality of spikes are inserted into the ground. In fact, both the resistance and capacitance of the soil vary with moisture and vary independently of each other depending upon soil condition. The relation of resistance to moisture particularly is non-linear and very difficult to predict for any given composition. Devices which ignore variation of resistance with capacitance necessarily produce an inaccurate indication of moisture content.

U.S. Pat. No. 4,288,742 to Walsh discloses a unique, simple, and effective moisture sensor which can be inserted easily into material to be measured, usually without damage to that material, and which takes into account both resistance and capacitance to produce an accurate indication of moisture content. The sensor includes a probe having at least a single, and preferably a plurality of spines extending outward from a base so that the spines can be inserted into the material. The spines are sufficient in number to appear as a ground plane forming an effective coaxial capacitor. Inaccuracies resulting from fringing fields are eliminated while the device remains easily insertable.

The impedance produced by the material surrounding the spines forms part of an RC bridge, preferably a Wien or other bridge, which also includes a separate resistor and capacitor. Thus, the impedance of the material, both its capacitance and resistance, are measured to produce signals indicating that impedance. By determining the ratio of the voltages across the RC circuit forming part of the bridge and the RC circuitry of the material impedance and determining the resonant frequency, both the resistance and capacitance of the soil can be determined and related to the dielectric constant of the material. From that dielectric constant the soil moisture content can be easily determined according to well known relations.

The coaxial geometry of the device accurately defines the active volume by minimizing fringe volumes. With sensors of the type which use plates, the fringe capacitances introduce errors since those capacitances vary with the dielectric constant. The coaxial geometry has no such fringe capacitance, except at the ends. A first ring of spines extend outwardly from a base in parallel with a second ring of spines extending outwardly from the base, also in parallel, and within the first ring, separated and insulated electrically therefrom. The two rings thus form an effective coaxial capacitor which can be inserted into the material to be sensed.

U.S. Pat. No. 4,540,936, also to Walsh, describes an improved moisture sensor. In one embodiment described in the Walsh patent, two slotted cylindrical tubes are mounted coaxially and replace the spines described in the above mentioned application. The cylindrical tubes are mounted coaxially and replace the spines described in the above mentioned application. The cylinders are sharpened on the end which pushes into the ground. A simple insulating plug is used to mount and electrically separate the two sensors.

In a second embodiment the volume is partially bounded by a cross shaped member having flat surfaces defining the volume in cross section as a square center with a rectangular leg extending from each side thereof. Each leg is open at the peripheral edge. The member and the volume in the legs tapers in the longitudinal direction so that at the insertion end the volume is made up only of the center section. A plurality of parallel plate capacitors are thereby formed by the parallel facing surfaces which are driven at the same potential. The four legs provide not only a controlled volume but good mechanical rigidity. The outer part of each leg can be insulated from the rest of the member is desired to serve as a guard ring.

In a third embodiment two cross-shaped members are jointed together at the peripheral edge of one leg of each. This gives better definition of the electrical volume since more of the volume is remote from openings and therefore less susceptible to fringe effects.

The sensors described by Walsh in U.S. Pat. No. 4,540,936, however, have several disadvantages. One of the described circuits requires variable resistors and capacitors, a variable frequency oscillator, a frequency detector, and an AC meter. These components add considerably to the cost, size, and complexity of the circuit. During the measurement process, the variable frequency oscillator must be swept through a range of frequencies in order to determine the resonant frequency. In general, the variable resistor and capacitor also must be adjusted during the measurement process. This makes the measurement process very complicated.

Another of the Walsh embodiment avoids the problems and difficulties associated with using frequency detectors, variable frequency oscillators, variable resistors and capacitors. However, it requires the use of an operational amplifier which is difficult at frequencies much in excess of 1 MHz as well as synchronous switches and a 90 degree phase shifter. In practice, considerable difficulty is involved in properly tuning the synchronous switches and in ensuring that the 90 degree phase shiftier produces a precise 90 degree phase shift. These components are also generally expensive and large. Finally, all three outputs, vout, er, and ei are AC voltages requiring AC meters.

It is accordingly an object of the present invention to provide an improved soil moisture sensor having circuitry which avoids the deficiencies of the Walsh patent as well as other prior art.

It is a further object of the invention to provide improved circuitry for a soil moisture sensor which is more compact and less expensive than previous designs.

DETAILED DESCRIPTION OF THE INVENTION

In accordance with the present invention, an improved circuitry is provided which is particularly adapted for use in a soil moisture sensor of the type disclosed, for example, in U.S. Pat. No. 4,540,936. The invention further includes a soil moisture sensor comprising a base with a capacitor extending outward to define adjacent extending surfaces at least partially bounding a volume containing the soil or other medium whose moisture content is being determined. The improved circuitry of the invention is connected to the capacitor, which may be coaxial, and provides an AC signal which measures the impedance between the surfaces of the capacitor by means of volt meters disposed in the circuit.

Figure 2:
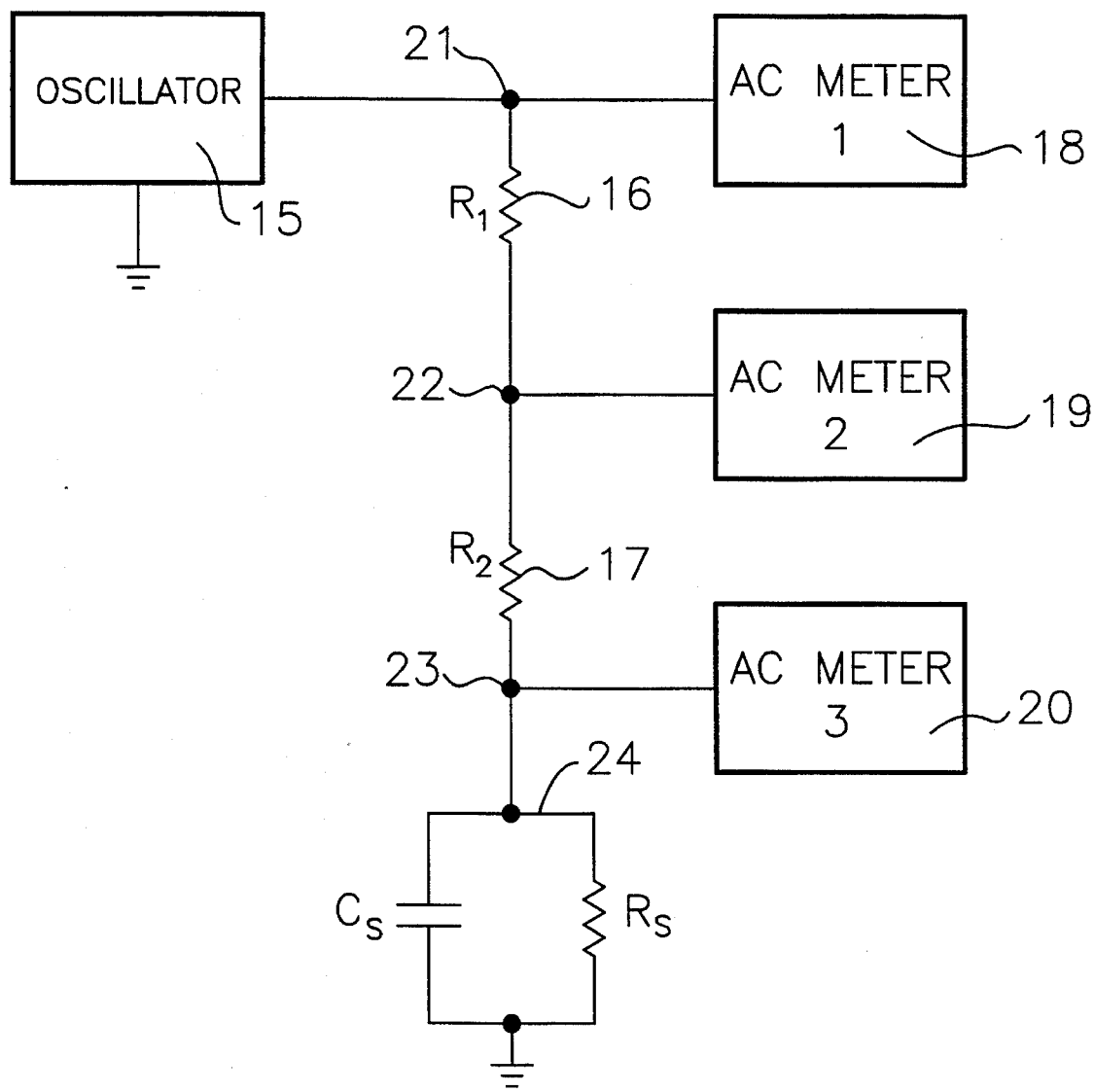
FIG. 2 is a schematic drawings showing one of the circuits used in the invention.

In one embodiment of the circuit, which is illustrated in FIG. 2 of the drawings, an oscillator 15 is used to apply an AC stimulus to two resistors (16 and 17) in series connected to a probe structure with an electrical impedance characterized by a sample capacitance, Cs, and resistance, Rs. Three meters 18, 19 and 20 are used to measure the voltage of the AC stimulus at three distinct points in the circuit: 21 between the oscillator 15 and resistor 16, between resistor 16 and resistor 17 (point 22), and between resistor 17 and probe 24 (point 23). The resulting output of the meters produced by this bridge structure can be directly related to Cs and Rs. In one embodiment where resistors 16 and 17 are of equal magnitude, R, the sample capacitance and resistance are given by:

$$C_s = \frac{\sqrt{8B^2A^2 + 8A^2 + 2B^2 - 16A^4 - B^4 - 1}}{4RB^2\omega}$$

$$R_s = \frac{4RB^2}{4A^2 - 3B^2 - 1}$$

where A and B are defined, respectively, as the ratio of the meter 19 output to the meter 18 output and the ratio of the meter 20 output of the meter 18 output and ω is 2π times the frequency of the AC stimulus. Other embodiments of the circuit employ both a resistor and capacitor, in parallel, in place of both resistors 16 and 17, in which case the relations for Cs and Rs above are different.

Figure 3:
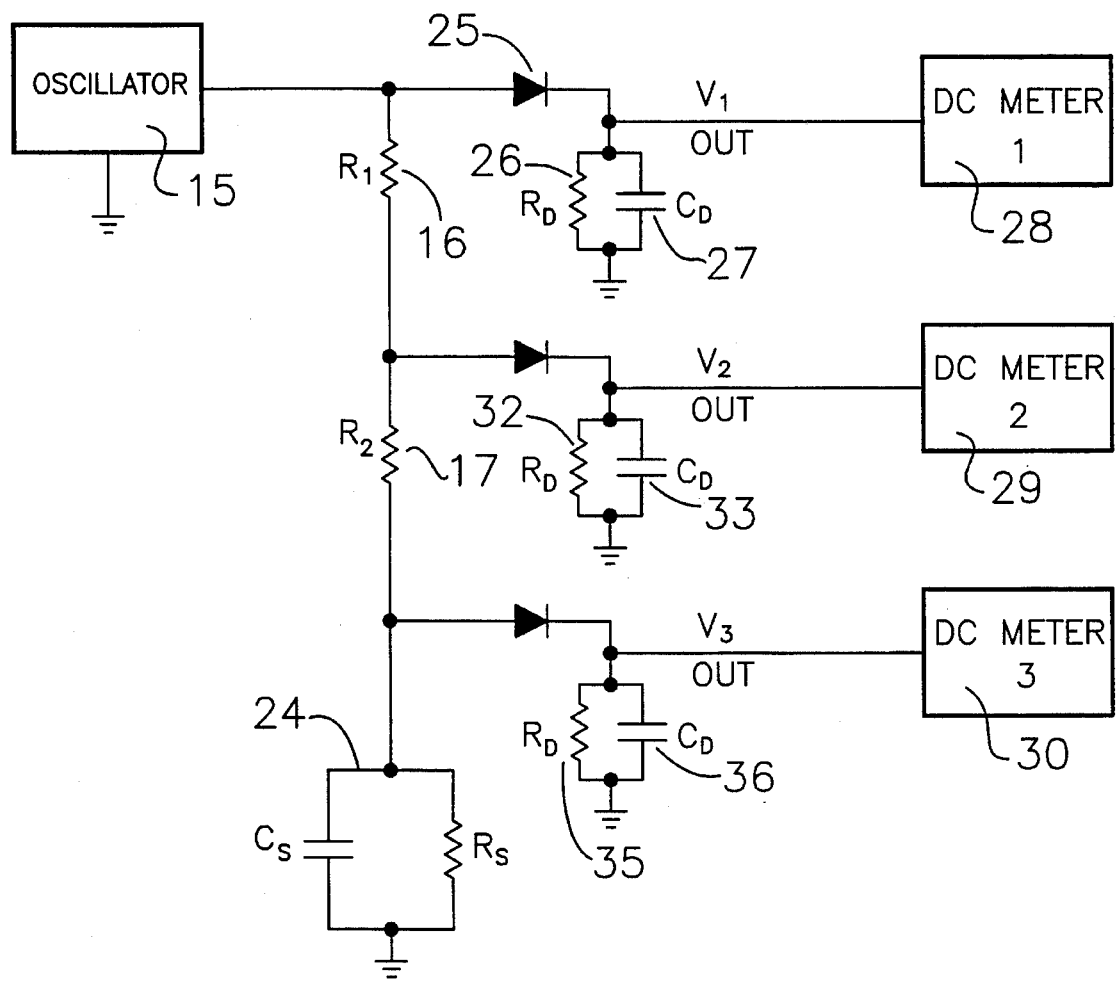
FIG. 3 is schematic drawing showing another of the circuits of the invention.

In another embodiment of the invention shown in FIG. 3 of the drawings, the AC meters of the embodiment shown in FIG. 2 have been replaced with diode 25 in series with a resistor, $R_D$, and capacitor, $C_D$, in parallel. AC meter 18 in FIG. 2 has been replaced with diode 25, resistor 26, capacitor 27 and DC meter 28. DC meter 28 is then used to measure the voltage at a point between the diode 25 and resistor 26, indicated at $V_1$. The DC meters may be separated by a considerable distance from the rest of the circuit. The relation of the output voltages, after correction for a small voltage drop across the diode, to the sample resistance and capacitance is identical to the previous embodiment employing AC meters.

Typically, AC stimulus frequencies between 1 and 100 MHz are employed. At these frequencies, AC meters are significantly more complicated than DC meters. In addition, at these frequencies, coaxial cable must be used to connect the AC meters to the circuit if they are to be any significant distance (1" or greater) from the rest of the circuit. Coaxial cable itself has an intrinsic capacitance that can easily be much larger than the probe structure. This introduces significant error and difficulty to the determination of sample resistance and capacitance.

The embodiment illustrated in FIG. 3 thus has the following advantages over the FIG. 2 embodiment. The FIG. 3 embodiment requires simpler DC meters as opposed to the more problematic AC meters in the FIG. 2 embodiment. In addition, since the output voltages in the FIG. 3 embodiment are DC voltages, the voltages can be measured by DC voltmeters separated from the probe structure by simple wires (as opposed to coaxial cable) in excess of 100 feet without introducing the errors and difficulty associated with using coaxial cable.

The advantages in the FIG. 3 embodiment thus allow for inexpensive and small components to be used and the circuit (excluding the DC meters) to be compact in size and mounted directly on the probe structure. The entire circuit can then be completed by simple wires to DC voltmeters located at great distance from the probe without incurring the cost, measurement error, and difficulty associated with coaxial cable and AC meters.

This considerably broadens the utility of the sensing system. First a number of sensors can be multiplexed to the same DC voltmeter sharply reducing the cost of multiple sensor systems. In addition, the inexpensive probe/circuit sensor can be placed in environmentally hostile locations where AC meters may fail to properly operate or be damaged, or if a remotely located AC meter is employed, at distances such that coaxial cable effects preclude an accurate measurement. In principle, one could place the AC meters immediately adjacent to the rest of the circuit and mount this circuit onto the probe and read the AC meters from a considerable distance. However in practice the circuit becomes inconveniently large and much more expensive and sophisticated.

Figure 1:
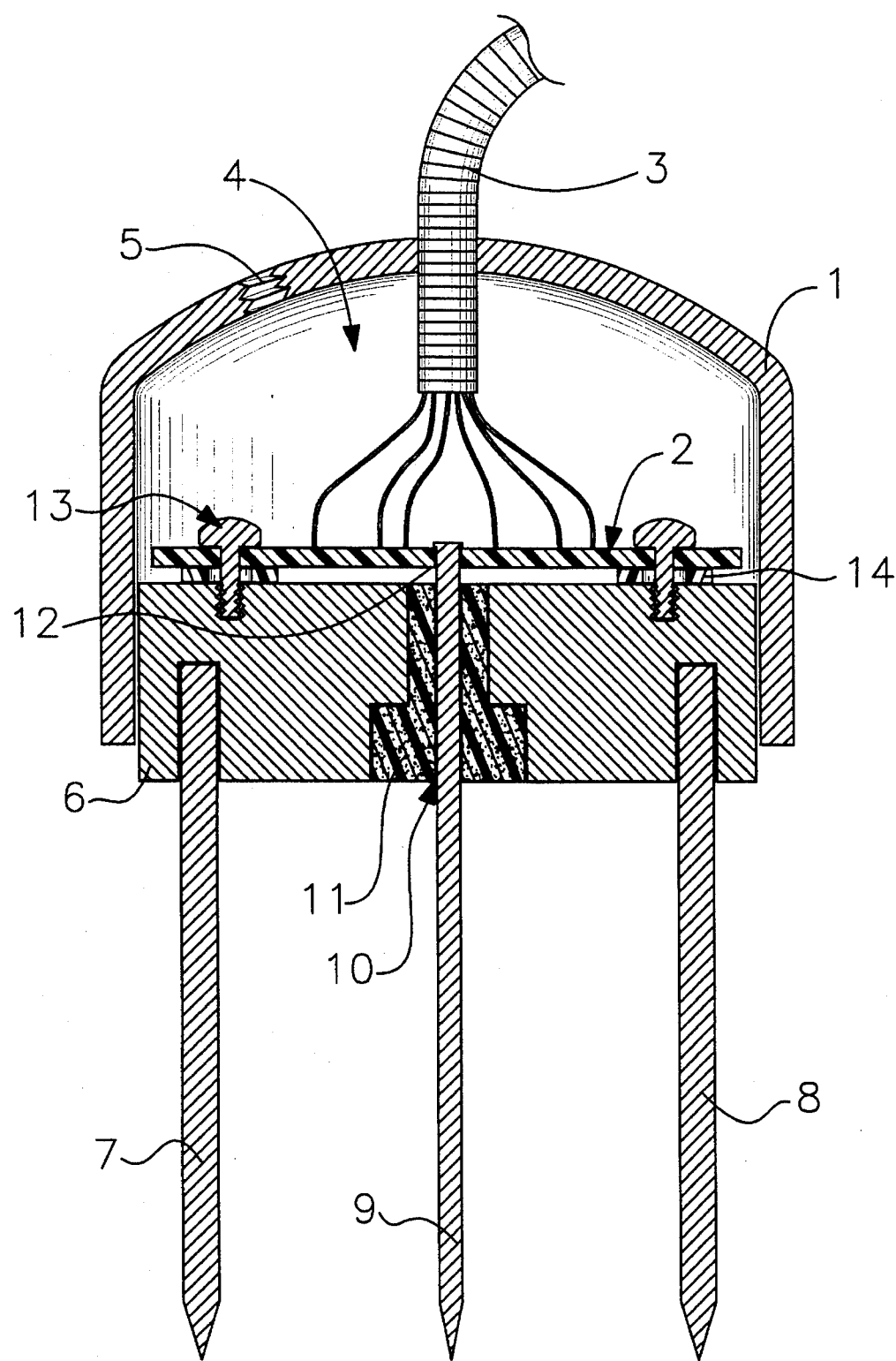
FIG. 1 is a side, cutaway view illustrating a soil moisture sensor incorporating the improved circuitry of the invention.

As already noted, the improved circuitry of the present invention, can advantageously be employed with any of the soil moisture sensors described in U.S. Pat. No. 4,540,936 or there equivalents. FIG. 1 of the drawings, illustrates a preferred embodiment of the present invention whereby the improved electrical circuitry is actually incorporated into the sensor head as a "sealed in" component of the unit. This eliminates the inaccuracy, difficulty and expense of using coaxial cable to connect the electrical circuit to the sensor spikes which form the capacitor which is inserted into the soil.

Directing attention to FIG. 1 of the drawings, the moisture sensor of the invention consists of an insulting, waterproof cap 1 which fits tightly over a base 6. A multiconductor cable 3 passes through the cap 1 to provide the necessary electrical current to the oscillator 15 and to connect the system with the associated volt meters used to register resistance and capacitance. Conventionally, the void space between the top of the protective cap 1, which may be made for example of polyvinyl chloride, and the circuit board 2 is filled with epoxy resin 4 or similar material through a plugged hole 5. This increases the mechanical strength of the assembly and prevents water or other contaminants from deleteriously affecting the circuit. The circuit board 2 contains the electrical circuit to the invention as illustrated in FIGS. 2 and 3 of the drawings, excepting the meters and recording equipment which are remotely attached through cable 3 as well as the electric power source for supplying electric stimulus to the system. Two sets of conductive tines or spikes are provided to form the capacitor which is inserted into the soil or other material being tested. The central conductive spike 9 is connected to the circuit board at 12 and forms one of the capacitor plates. Spike 9 passes through electrically insulating insert 11, which may be Teflon, and water tight seal 10 to emerge from the base of the sensor head and connect with the circuitry. A plurality of additional spikes or tines 7 and 8 are pressure fitted into the base 6 and then appropriately connected to the circuit board to form the other plate of the capactior. Conveniently, this connection may be to screws 13 which hold the circuit board to the base member 6. It will be appreciated that any number of tines 7, 8 may be similarly disposed around the perimeter of the sensor head to form the outer surrounding capacitor surface which is inserted into the material along with the central tine 9. Typically, for example, three such outer or peripheral tines may be equally disposed around the central tines 9 although a greater number may also be employed. As an alternative means of connecting the outer tines with the circuit board, the base 6 may be made of a conducting material which is thereby connected by means of screw 13 with the appropriate portions of the circuit board 2. Shorting out the circuit board with the conductive base 6 is avoided by providing stands offs 14 which physically separate the bottom of the circuit board and the base 6. Similarly the central tine 9 is prevented from making electrical contact with the conductive base 6 by means of the teflon insert 11 which prevents contact between the tine 9 and base 6.

As thus assembled, or in its equivalent form, the moisture sensor of the present invention, will be seen to have the advantage of ease of assembly, water tight and corrosion resistant construction, light weight and simplicity of design. Without the need for extensive external equipment as described in U.S. Pat. No. 4,540,936, the moisture sensor of the present invention, with its improved electrical circuity offers a much less expensive, more accurate, simplified and easy to use unit for determining soil or other material moisture or salinity.

It will be apparent to those of ordinary skill in the art that various modifications both in the specific structure described herein and in equivalent structures illustrated in the prior art can as well be used in accordance with the present invention and are considered to fall within scope thereof.

I claim:

1. A moisture sensor for insertion into a moisture containing media to determine the amount of said moisture by measuring the capacitance and resistance of said media comprising: a base for maintaining in alignment probe means which extend outwardly from said base including a plurality of elongated conductors disposed around a centrally disposed elongated conductor to form an effective coaxial capacitor defining adjacent extending surfaces partially bounding at least one volume containing said media when said moisture sensor is inserted in said media; and circuit means connected to said probe means extending outwardly for applying an ac signal thereto to measure the electrical impedance between said bounding surfaces and thereby determine the moisture content and salinity of said media; said circuit means comprising: oscillator means for applying electric stimulus to a pair of resistors connected in series to probe means for registering impedance of the material into which said probe means is placed; and separate voltage measuring means, $M_1$, $M_2$ and $M_3$, placed respectively between said oscillator means and the first of said resistors between said resistors and between said probe means and the second of said resistors; said electrical impedance being characterized by the capacitance and resistance of said material, which capacitance and resistance is a function of the voltage, $V_1$, $V_2$ and $V_3$ measured respectively by said voltage measuring means $M_1$, $M_2$, and $M_3$ and the frequency of said electric stimulus and permitting calculation of said amount of moisture.

2. The sensor of claim 1 wherein said voltage measuring means are AC volt meters and said electric stimulus is AC.

3. The sensor of claim 1 wherein each of said voltage measuring means comprises a diode detector in series with a D.C. volt meter.

4. The sensor of claim 3 wherein said diode detectors each consist of a diode in series with a grounded resistor connected in parallel to a capacitor.

5. The sensor of claim 1 wherein both of said resistors have the same value, R, and said capacitance, $C_s$, is determined in accordance with the relationship:

$$C_s = \frac{\sqrt{8B^2A^2 + 8A^2 + 2B^2 - 16A^4 - B^4 - 1}}{4RB^2\omega}$$

said resistance, $R_s$ is determined in accordance with the relationship:

$$R_s = \frac{4RB^2}{4A^2 - 3B^2 - 1}$$

where A is the ratio $V_2/V_1$, B is the ratio $V_3/V_1$ and $\omega$ is $2\pi$ times the frequency of the stimulus.

\* \* \* \* \*